United States Patent [19]

Mathey et al.

[11] Patent Number: 6,037,493
[45] Date of Patent: Mar. 14, 2000

[54] OPTICALLY ACTIVE DIPHOSPHINES, PREPARATION THEREOF ACCORDING TO A PROCESS FOR THE RESOLUTION OF THE RACEMIC MIXTURE AND USE THEREOF

[75] Inventors: Francois Mathey, Paris; Frédéric Robin, Montrouge; Francois Mercier, Versailles; Michel Spagnol, Lyons, all of France

[73] Assignee: Rhone-Poulenc Chimie, Courbevoie Cedex, France

[21] Appl. No.: 09/025,441

[22] Filed: Feb. 17, 1998

Related U.S. Application Data

[62] Division of application No. 08/696,824, filed as application No. PCT/FR95/01716, Dec. 22, 1995.

[30] Foreign Application Priority Data

Dec. 28, 1994 [FR] France .................................. 94 15757
May 29, 1995 [FR] France .................................. 95 06286

[51] Int. Cl.[7] .................................... C07C 53/00
[52] U.S. Cl. ........................ 562/512; 562/480; 562/553
[58] Field of Search ................... 562/480, 553, 562/512; 568/17

[56] References Cited

U.S. PATENT DOCUMENTS

| | | | |
|---|---|---|---|
| 5,012,002 | 4/1991 | Kumobayashi | 556/21 |
| 5,231,202 | 7/1993 | Hayashi | 556/21 |
| 5,515,944 | 5/1996 | Broger | 568/13 |
| 5,559,267 | 9/1996 | Burk | 560/140 |

OTHER PUBLICATIONS

CA:121:57572—Abstract of "The equilibrium between 1H and 2H phopholes," Laporte, Bull Soc. Fr. 139(6), pp. 843–850.

CA:117:48704—Abstract of "Mechanism of the thermal tetramerization of phospholes," Bevierre<Bull Soc. Chem Fr., 129(1)pp 1–8.

Bevierre et al, "Mechanism of the thermal tetramerization of phospholes," Bull. Soc. Chim. Fr. (BSCFAS, 00378968), vol. 129 (1), pp. 1–8, EC Polytech. Lab. Chim. Phosphore Met. Transition, Palaiseau, 91128 (FR), (1992).

*Primary Examiner*—Gary Geist
*Assistant Examiner*—Jean F Vollano
*Attorney, Agent, or Firm*—Burns, Doane, Swecker & Mathis, L.L.P.

[57] ABSTRACT

The present invention relates to optically active diphosphines. It is also targeted at their preparation according to a process for the resolution of the racemic mixture of the said phosphines to optically active isomers.

The subject of the invention is new optically active bis[1-phospha-2,3-diphenyl-4,5-dimethylnorbornadiene] diphosphines and a process for resolving the racemic bis[1-phospha-2,3-diphenyl-4,5-dimethylnorbornadiene] mixture which comprises reacting it with a palladium or platinum complex as chiral auxiliary in an organic solvent, thus forming diastereoisomer complexes, and then resolving the said optically pure complexes.

The invention also relates to new optically active metal complexes comprising the said phosphines and to their use in a process for the preparation of optically active carboxylic acids and/or derivatives according to a process for the hydrogenation of α,β-unsaturated carboxylic acids and/or derivatives.

15 Claims, No Drawings

OPTICALLY ACTIVE DIPHOSPHINES, PREPARATION THEREOF ACCORDING TO A PROCESS FOR THE RESOLUTION OF THE RACEMIC MIXTURE AND USE THEREOF

This application is a divisional of application Ser. No. 08/696,824, filed Oct. 4, 1996, which is a 371 of PCT Application No. PCT/FR95/01716, filed Dec. 22, 1995.

The present invention relates to optically active diphosphines. It is also targeted at their preparation according to a process for the resolution of the racemic mixture of the said phosphines to optically active isomers.

More precisely, the subject of the invention is new optically active bis[1-phospha-2,3-diphenyl-4,5-dimethylnorbornadiene] diphosphines and the process for the resolution of the racemic bis[1-phospha-2,3-diphenyl-4,5-dimethylnorbornadiene] mixture.

The invention also relates to new optically active metal complexes comprising the said phosphines and to their use in a process for the preparation of optically active carboxylic acids and/or derivatives according to a process for the hydrogenation of α,β-unsaturated carboxylic acids and/or derivatives. The preparation of a mixture of bis [1-phospha-2,3-diphenyl-4,5-dimethylnorbornadiene] diastereoisomers has been described by F. Mathey et al. in Bull. Soc. Chim. Fr., 129, pp. 1–8 (1992).

The starting material in the synthesis of the latter is 1-phenyl-3,4-dimethylphosphole (II) described by F. Mathey et al. in Synthesis, 1983, pp. 983.

The starting point is the preparation of 3,3',4,4'-tetramethyl-1,1'-diphosphole (IV). To this end, 1-phenyl-3,4-dimethylphosphole (II) is reacted in THF with lithium metal according to the following reaction:

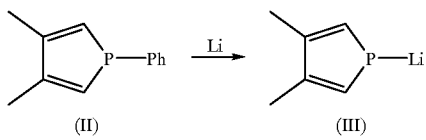

At the end of the reaction, aluminium chloride is introduced in order to trap the phenyllithium produced during the reaction.

In a following stage, (III) is dimerized by the action of diiodine $I_2$ in THF. For more details on the preparation of (IV), reference may be made to the article by F. Mathey et al., Organometallics, 1983, 2, 1234.

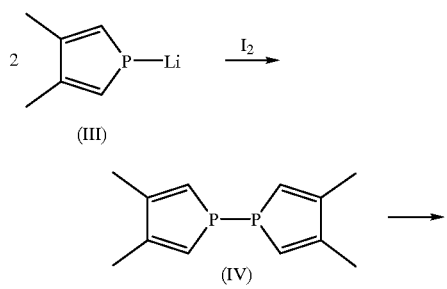

On heating to approximately 140° C., the compound (IV) rearranges to (V), which reacts with diphenylacetylene according to the Diels-Alder reaction, to give bis[1-phospha-2,3-diphenyl-4,5-dimethylnorbornadiene].

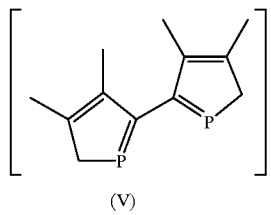

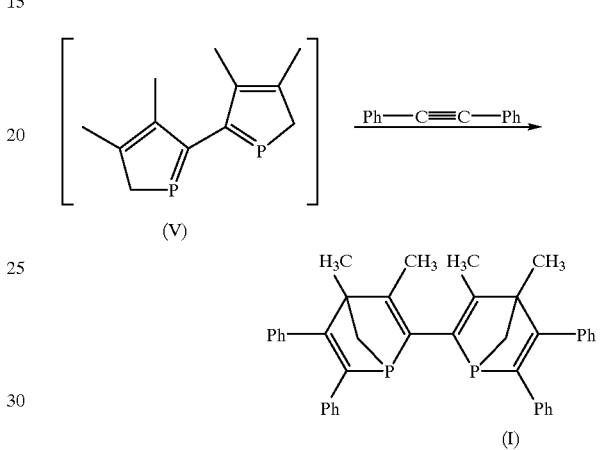

A practical embodiment is given on page 6 of the publication by F. Mathey et al. in Bull. Soc. Chim. Fr., 129, pp. 1–8 (1992).

However, the writers obtained, as mentioned on page 3, right-hand column, lines 7 and 8, a mixture of two diastereoisomers subsequently identified by the Applicant Company as being a meso (I m)—RS,SR—and a racemate (I r)—RR,SS—called (13b) and (13a) respectively in the article.

The publication mentions the separation of the two diastereoisomers by formation of a palladium(II) chelate. To do this, a description is given of the separation of the mixture of diastereoisomers obtained by reaction with $PdCl_2$ $(PhCN)_2$ in dichloroethane, resulting in (VI m) and (VI r), and the separation by chromatography on silica gel, followed by elution and then by a decomplexation carried out by NaCN.

The two diastereoisomers, on the one hand the meso (I m) and, on the other hand, the racemate (I r), are thus recovered separately.

The document of the state of the art does not describe the separation of the enantiomers.

The problem of resolving two enantiomers is difficult to solve when the chirality is carried by the phosphorus.

An object of the present invention is to provide new, bidentate, optically active disphosphines which are chiral on the phosphorus and which cannot be racemized.

Another object of the present invention is to make available a process which makes it possible to obtain them according to a process for resolving the racemic bis[1-phospha-2,3-diphenyl-4,5-dimethylnorbornadiene] mixture.

Finally, another object of the invention is to have available a process for the preparation of optically active carboxylic acids and/or derivatives according to a process for the hydrogenation of α,β-unsaturated carboxylic acids and derivatives which makes use of metal complexes using the optically active diphospine as ligand.

According to a first subject of the present invention, new optically active bis[1-phospha-2,3-diphenyl-4,5-dimethylnorbornadiene] diphosphines have been found which correspond to the following formulae:

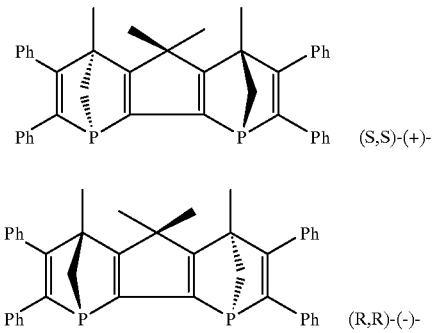

According to another subject of the invention, the racemic bis[1-phospha-2,3-diphenyl-4,5-dimethylnorbornadiene] mixture is resolved according to a process which comprises reacting it with a palladium and/or platinum complex as chiral auxiliary in an organic solvent, thus forming diastereoisomer complexes, and then resolving the said optically pure complexes.

In accordance with the process of the invention, a palladium complex is used. This type of chiral auxiliary is widely described in the literature, in particular by Sei Otsuka et al. in Journal of the American Chemical Society, 93, pp. 4301 (1971).

A platinum complex can also be used and reference may more particularly be made to the work by A. C. Cope [Journal of the American Chemical Society, 90, pp. 909 (1968)].

The chiral complex used more particularly corresponds to the general formula (VII):

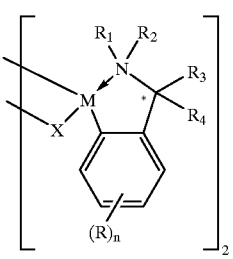

in the said formula:

M represents palladium and/or platinum, $R_1$, $R_2$, $R_3$ and $R_4$ represent a hydrogen atom or an alkyl radical having from 1 to 10 carbon atoms or a cycloalkyl radical having from 3 to 10 carbon atoms, $R_3$ and $R_4$ are different and at least one of the two represents a hydrogen atom, R has the meaning given for $R_1$, $R_2$, $R_3$ and $R_4$, x represents a halogen atom, n is a number from 0 to 4, when n is greater than 1, two R radicals and the 2 successive atoms of the benzene ring can form, between them, a ring having from 5 to 7 carbon atoms.

More preferentially, the complex used corresponds to the abovementioned formula in which $R_1$, $R_2$, $R_3$ and $R_4$ represent a hydrogen atom or a methyl radical, X represents a chlorine atome and n is equal to 0.

When n is equal to 2, two R radicals form a benzene ring.

Mention may be made, as more specific examples of palladium complexes which are suitable for the present invention, obtained without distinction from (R)-(+)- or (S)-(−)-N,N-dimethylphenylethylamine, of:

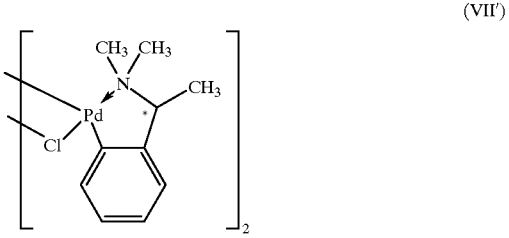

The amount of complex of the abovementioned metals, expressed as metal, is generally from 0.5 to 1 metal atom per phosphorus atom.

An organic solvent is used which dissolves all the reactants. The solvent must be inert with respect to the diphosphine.

Mention may be made, as non-limiting examples of solvents which are suitable in the process of the invention, of:

aliphatic hydrocarbons and more particularly paraffins such as, in particular, pentane, hexane, heptane, octane, isooctane, nonane, decane, undecane, tetradecane, petroleum ether and cyclohexane; aromatic hydrocarbons such as, in particular, benzene, toluene, xylenes, ethylbenzene, diethylbenzenes, trimethylbenzenes, cumene, pseudocumene or petroleum fractions composed of a mixture of alkylbenzenes, in particular fractions of Solvesso® type, halogenated aliphatic or aromatic hydrocarbons, and mention may be made of: perchlorinated hydrocarbons such as, in particular, trichloromethane or tetrachloroethylene; partially chlorinated hydrocarbons, such as dichloromethane, dichloroethane, tetrachloroethane, trichloroethylene, 1-chlorobutane or 1,2-dichlorobutane; or monochlorobenzene, 1,2-dichlorobenzene, 1,3-dichlorobenzene, 1,4-dichlorobenzene or mixtures of different chlorobenzenes.

Benzene and toluene are preferred among all these solvents.

The concentration of the diphosphine in the 15 reaction solvent is preferably between 0.05 and 1 mol/liter and more particularly still between 0.05 and 0.2 mol/liter.

Separation is advantageously carried out at ambient temperature, generally between 15° C. and 25° C.

It preferably takes place under a controlled atmosphere of inert gases. A rare gas atmosphere, preferably of argon, can be set up but it is more economical to use nitrogen.

A mixture of complexes of palladium or platinum and of diphosphine corresponding to each enantiomer is obtained.

Another subject of the invention is the intermediate product, namely the metal complex with the diphosphines of formula:

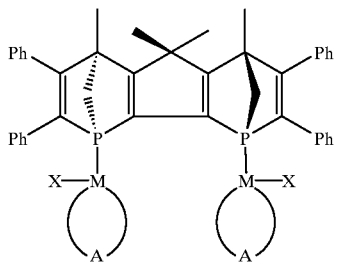

(VIII a)

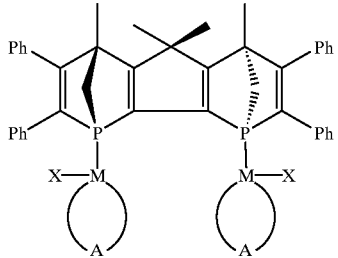

(VIII b)

in the said formulae M represents palladium or platinum, X a halogen atom, preferably chlorine, and A symbolizes the residue of a chiral metal complex corresponding to one of the formulae (VII) and preferentially (VII').

The two pure enantiomers are recovered in a following stage.

The solvent is concentrated by evaporation and separation is then carried out in a known way [A. Bertheillier-Dunod Paris (1972)] by liquid chromatography on a column with, preferably, a support made of silica.

The column is eluted with a mixture of suitable solvents, preferably a toluene/ethyl acetate mixture preferentially comprising 80% by volume of toluene and 20% by volume of ethyl acetate.

The two pure isolated enantiomers are recovered in the form of two diastereoisomer complexes having the following characteristics:

$^{31}P$ NMR=δ(CH$_2$Cl$_2$)=55.9 ppm
$^{31}P$ NMR=δ(CH$_2$Cl$_2$)=53.6 ppm

The two pure enantiomers of the diphosphine are recovered by carrying out decomplexation.

To this end, use is made in particular of a hydrocyanic acid salt, preferably an alkali metal salt and more preferentially still the sodium salt: the said salt being dissolved in the minimum amount of water necessary.

The complexes are dissolved in an organic solvent such as, for example, dichloromethane and then the hydrocyanic acid salt, generally used in an excess representing from 2 to 5 mol per metal atom, is introduced with stirring.

The operation is also carried out under a controlled atmosphere and at ambient temperature.

The enantiomer is recovered in the organic phase, which phase is separated, washed with water and dried, for example over sodium sulphate.

The two pure isolated enantiomers of bis[1-phospha-2,3-diphenyl-4,5-dimethylnorbornadiene] corresponding to the abovementioned formulae [(S,S)-(+)-(Ia)] and [(R,R)-(−)-(Ib)] are obtained, the characteristics of which are as follows:

$^{31}P$ NMR=δ(CDCl$_3$)=−13.2 ppm; [α]$_D$=+231° (c=1, C$_6$D$_6$).

$^{31}P$ NMR=δ(CDCl$_3$)=−13.2 ppm; [α]$_D$=−198° (c=1, C$_6$D$_6$)

(with an [α]$_D$ determined for a concentration of 10 mg/ml and at ambient temperature).

It has also been found, which constitutes another subject of the present invention, that the new optically active diphosphines as mentioned above in the form of metal complexes could be used as catalysts for the asymmetric hydrogenation of a,-unsaturated carboxylic acids and/or derivatives.

The optically active diphosphines of formula (Ia) or (Ib) are used as ligands in the formation of complexes with transition metals.

A subject of the invention is therefore new complexes comprising an optically active diphosphine and a transition metal which are characterized in that the ligand corresponds to one of the following formulae:

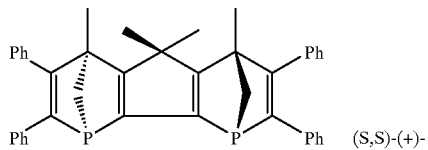

(Ia)

(S,S)-(+)-

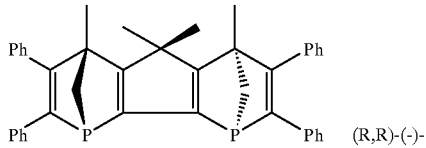

(Ib)

(R,R)-(−)-

Mention may be made, as examples of transition metals capable of forming complexes, of in particular metals such as rhodium, ruthenium, rhenium, iridium, cobalt, nickel, platinum or palladium.

Rhodium, ruthenium and iridium are preferred among the abovementioned metals.

Specific examples of the said complexes of the present invention are given hereinbelow, without limiting nature.

In the said formulae, (P*P) represents the diphosphine of formula (Ia) or (Ib).

The rhodium and iridium complexes can be represented by the following formulae:

[M L$_2$(P*P)]Y     (IIa)

[M L$_2$(P*P)]Y     (IIb)

in the said formulae:
(P-P) represents, in the formula (IIa), the diphosphine of formula (Ia) and, in the formula (IIb), the diphosphine of formula (Ib),
M represents rhodium or iridium,
Y represents an anionic coordinating ligand,
L represents a neutral ligand.

The preferred rhodium or iridium complexes correspond to the formula (IIa) or (IIb) in which:
L represents an olefin having from 2 to 12 carbon atoms and two L ligands can be joined to one another in order to form a linear or cyclic polyunsaturated hydrocarbon chain; L preferably representing 1,5-cyclooctadiene, norbornadiens or ethylene,
Y represents a PF$_6^-$, PCl$_6^-$, BF$_4^-$, BC$_{14}^-$, SbF$_6^-$, SbCl$_6^-$, BPh$_4^-$, ClO$_4^-$, CN$^-$ or CF$_3$SO$_3^-$ anion, halogen, preferably Cl$^-$ or Br$^-$, a 1,3-diketonate, alkylcarboxylate or haloalkylcarboxylate anion with a lower alkyl radical, or a phenylcarboxylate or phenoxide anion in which the benzene ring can be substituted by lower alkyl radicals and/or halogen atoms.

The term lower alkyl radicals is generally understood to mean a linear or branched alkyl radical having from 1 to 4 carbon atoms.

Other iridium complexes can be represented by the formulae:

$$[IrL(P*P)]Y \quad (IIIa)$$

$$[IrL(P*P)]Y \quad (IIIb)$$

in the said formulae (P*P), L and Y have the meanings given for the formulae (IIa) and (IIb).

As regards the ruthenium complexes, they preferentially correspond to the following formulae:

$$[RuY_1Y_2(P*P)] \quad (IVa)$$

$$[RuY_1Y_2(P*P)] \quad (IVb)$$

in the said formulae:
(P*P) represents, in the formula (IVa), the diphosphine of formula (Ia) and, in the formula (IVb), the diphosphine of formula (Ib), $Y_1$ and $Y_2$, which are identical or different, preferably represent a $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$ anion, a halogen atom, more particularly chlorine or bromine, or a carboxylate anion, preferentially acetate or trifluoroacetate.

Other ruthenium complexes capable of being used in the process of the invention correspond to the formulae hereinbelow:

$$[RuY_1Ar(P*P)Y_2] \quad (IVc)$$

$$[RuY_1Ar(P*P)Y_2] \quad (IVd)$$

in the said formulae:
(P*P) represents, in the formula (IVc), the diphosphine of formula (Ia) and, in the formula (IVd), the diphosphine of formula (Ib), Ar represents benzene, p-methylisopropylbenzene or hexamethylbenzene, $Y_1$ represents a halogen atom, preferably chlorine or bromine, $Y_2$ represents an anion, preferably a $PF_6^-$, $PCl_6^-$, $BF_4^-$, $BCl_4^-$, $SbF_6^-$, $SbCl_6^-$, $BPh_4^-$, $ClO_4^-$ or $CF_3SO_3^-$ anion.

It is also possible to use complexes based on palladium and on platinum in the process of the invention.

Mention may be made, as more specific examples of the said complexes, of, inter alia, $PdCl_2(P*P)$ and $PtCl_2(P*P)$ in which (P*P) represents the diphosphine of formula (Ia) or (Ib).

The complexes comprising the abovementioned diphosphine and the transition metal can be prepared according to the known processes described in the literature.

For the preparation of the ruthenium complexes, reference may in particular be made to the publication by J. -P. Genêt [Acros Organics Acta, 1, No. 1, pp. 1–8 (1994)] and, for the other complexes, to the article by Schrock R. and Osborn J. A. [Journal of the American Chemical Society, 93, pp. 2397 (1971)].

They can be prepared in particular by reaction of the diphosphine of formula (Ia) or (Ib) with the transition metal compound in a suitable organic solvent.

The reaction is carried out at a temperature of between ambient temperature (from 15 to 25° C.) and the reflux temperature of the reaction solvent.

Mention may be made, as examples of organic solvents, of, inter alia, halogenated or non-halogenated aliphatic hydrocarbons and more particularly hexane, heptane, isooctane, decane, benzene, toluene, =ethylene chloride or chloroform;

solvents of ether or ketone type and in particular diethyl ether, tetrahydrofuran, acetone or methyl ethyl ketone; or solvents of alcohol type, preferably methanol or ethanol.

The metal complexes according to the invention, recovered according to conventional techniques (filtration or crystallization), are used in reactions for the asymmetric hydrogenation of substrates specified hereinbelow.

Another object of the present invention is to provide a process for the preparation of an optically active carboxylic acid and/or derivative, which process is characterized in that an α,β-unsaturated carboxylic acid and/or its derivatives is/are asymmetrically hydrogenated in the presence of an effective amount of a metal complex comprising, as ligand, the optically active diphosphine of formula (Ia) or (Ib) and a transition metal.

The α,β-unsaturated carboxylic acid and/or its derivatives corresponds more particularly to the formula (V):

$$\begin{array}{c} R_1 \\ \diagdown \\ R_2 \end{array} = \begin{array}{c} COOR_4 \\ \diagup \\ R_3 \end{array} \quad (V)$$

in the said formula (V):

$R_1$, $R_2$, $R_3$ and $R_4$ represent a hydrogen atom or any hydrocarbon group, insofar as:

if $R_1$ is other than $R_2$ and other than a hydrogen atom, then $R_3$ can be any functional or hydrocarbon group denoted by R.

if $R_1$ or $R_2$ represents a hydrogen atom and if $R_1$ is other than $R_2$, then $R_3$ is other than a hydrogen atom and other than —$COOR_4$, if $R_1$ is identical to $R_2$ and represents any functional or hydrocarbon group denoted by R, then $R_3$ is other than —CH—$(R)_2$ and other than —$COOR_4$, it being possible for one of the $R_1$, $R_2$ and $R_3$ groups to represent a functional group.

The $R_1$ to $R_4$ radicals, which are identical or different, represent an optionally substituted hydrocarbon radical having from 1 to 20 carbon atoms which can be a linear or branched, saturated or unsaturated, acyclic aliphatic radical; a monocyclic or polycyclic, saturated, unsaturated or aromatic, heterocyclic or carbocyclic radical; or a linear or branched, saturated or unsaturated, aliphatic radical carrying a cyclic substituent.

In the general formula (V), $R_1$ to $R_4$, which are identical or different, can take various meanings. Different examples are given hereinbelow but they are in no way limiting.

Thus, the $R_1$ to $R_4$ radicals preferentially represent an aromatic hydrocarbon, and in particular benzene, radical corresponding to the general formula (V'):

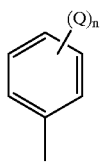

(V')

in the said formula (V'):
n is an integer from 0 to 5, preferably from 0 to 3;
Q represents $R_0$, one of the following groups or functional groups:
a linear or branched alkyl radical having from 1 to 6 carbon atoms, preferably from 1 to 4 carbon atoms, such as methyl, ethyl, propyl, isopropyl, butyl, isobutyl, sec-butyl or tert-butyl,
a linear or branched alkenyl radical having from 2 to 6 carbon atoms, preferably from 2 to 4 carbon atoms, such as vinyl or allyl,
a linear or branched alkoxy radical having from 1 to 6 carbon atoms, preferably from 1 to 4 carbon atoms, such as methoxy, ethoxy, propoxy, isopropoxy and butoxy radicals,
an acyl group having from 2 to 6 carbon atoms,
a radical of formula:
—$R_5$—OH
—$R_5$—COO$R_7$
—$R_5$—CHO
—$R_5$—NO$_2$
—$R_5$—CN
—$R_5$—N($R_7$)$_2$
—$R_5$—CO—N($R_7$) 2
—$R_5$—SH
—$R_5$—X
—$R_5$—CF$_3$
in the said formulae $R_5$ represents a valence bond or a saturated or unsaturated, linear or branched, divalent hydrocarbon radical having from 1 to 6 carbon atoms such as, for example, methylene, ethylene, propylene, isopropylene or isopropylidene; $R_7$ represents a hydrogen atom or a linear or branched alkyl radical having from 1 to 6 carbon atoms; and X symbolizes a halogen atom, preferably a chlorine, bromine or fluorine atom.
Q represents $R_0'$, one of the following, more complex radicals:

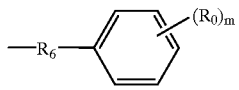

in which:
m is an integer from 0 to 5, preferably from 0 to 3,
$R_0$ has the meaning give above,
$R_6$ represents a valence bond; a saturated or unsaturated, linear or branched, divalent hydrocarbon group having from 1 to 6 carbon atoms such as, for example, methylene, ethylene, propylene, isopropylene or isopropylidene or one of the following groups known as Z:
—O—; —CO—; —COO—; —N$R_7$—; —CO—N$R_7$—; —S—; —SO$_2$— or —N$R_7$—CO—;
in the said formulae $R_7$ represents a hydrogen atom or a linear or branched alkyl group having from 1 to 6 carbon atoms, preferably a methyl or ethyl radical.

When n is greater than 1, the Q radicals can be identical or different and 2 successive carbon atoms of the benzene ring can be joined to one another by a ketal bridge, such as the methylenedioxy or ethylenedioxy extranuclear radicals.
Preferably, n is equal to 0, 1, 2 or 3.
Among all the abovementioned $R_1$ to $R_4$ radicals, use is very preferentially made, in the process of the invention, of carboxylic acids or derivatives corresponding to the general formula (V) in which $R_1$ to $R_4$ represent an aromatic radical corresponding to the general formula (V') in which:
n is equal to 0, 1, 2 or 3,
Q represents one of the following groups or functional groups:
a hydrogen atom,
a linear or branched alkyl radical having from 1 to 4 carbon atoms,
a linear or branched alkoxy radical having from 1 to 4 carbon atoms,
a benzoyl group,
an —OH group,
a —CHO group,
an NH$_2$ group,
an NO$_2$ group,
a phenyl radical,
a halogen atom,
a CF$_3$ group.
More preferentially still, the compounds of formula (V) are chosen in which the Q radicals, which are identical or different, are a hydrogen atom, an alkyl radical having from 1 to 4 carbon atoms, a methoxy radical, a benzoyl group or an NO$_2$ group.
Mention may more specifically be made, as examples of $R_1$ to $R_4$ radicals corresponding to the formula (V), of phenyl, tolyl or xylyl, 1-methoxyphenyl and 2-nitrophenyl radicals and biphenyl, 1,1'-methylenebiphenyl, 1,1'-isopropylidenebiphenyl, 1,1'-carboxybiphenyl, 1,1'-oxybiphenyl and 1,1'-iminobiphenyl radicals: it being possible for the said radicals to be substituted by one or a number of Q radicals as defined above.
$R_1$ to $R_4$ can also represent a polycyclic aromatic hydrocarbon radical; it being possible for the rings to form, between themselves, ortho-fused and ortho- and peri-fused systems. Mention may more particularly be made of a naphthalene radical; it being possible for the said rings to be substituted by 1 to 4 $R_0$ radicals, preferably 1 to 3 Ro radicals, R. having the meanings stated above for the substituents of the aromatic hydrocarbon radical of general formula (V').
In the general formula (V) of the carboxylic acids, $R_1$ to $R_4$ can also represent a saturated carbocyclic radical or a carbocyclic radical which comprises 1 or 2 unsaturations in the ring and which generally has from 3 to 7 carbon atoms, preferably 6 carbon atoms, in the ring; it being possible for the said ring to be substituted by 1 to 5, preferably 1 to 3, $R_0$ radicals, $R_0$ having the meanings stated above for the substituents of the aromatic hydrocarbon radical of general formula (V')
Mention may be made, as preferred examples of $R_1$ to $R_4$ radicals, of cyclohexyl or cyclohexenyl radicals, optionally substituted by linear or branched alkyl radicals having from 1 to 4 carbon atoms.
As mentioned above, $R_1$ to $R_4$ can represent a linear or branched, saturated or unsaturated, acyclic aliphatic radical.
More precisely, $R_1$ to $R_4$ represent a linear or branched acyclic aliphatic radical preferably having from 1 to 12 carbon atoms which is saturated or which comprises one to a number of unsaturations in the chain, generally 1 to 3 unsaturations, which can be double bonds, which are simple or conjugated, or triple bonds.

The hydrocarbon chain can optionally be:
interrupted by one of the following Z groups:
—O—; —CO—; —COO—; —NR$_7$—; —CO—NR$_7$—; —S—; —SO$_2$— or —NR$_7$—CO—;
in the said formulae R$_7$ represents a hydrogen atom or a linear or branched alkyl group having from 1 to 6 carbon atoms, preferably a methyl or ethyl radical,
and/or a carrier of one of the following substituents:
—OH, —COOR$_7$, —CHO, —NO$_2$, —CN, —NH$_2$, —SR, —X or —CF$_3$,
R$_7$ having, in these formulae, the meaning given above.

It is also possible to use a carboxylic acid or derivative of formula (V) in which R$_1$ to R$_4$ represent a linear or branched, saturated or unsaturated, acyclic aliphatic radical which can optionally carry a cyclic substituent. Ring is understood to mean a saturated, unsaturated or aromatic heterocyclic or carbocyclic ring.

The acyclic aliphatic radical can be joined to the ring by a valence bond or by one of the abovementioned Z groups.

It is possible to envisage, as examples of cyclic substituents, cycloaliphatic, aromatic or heterocyclic substituents, in particular cycloaliphatic substituents comprising 6 carbon atoms in the ring or benzene substituents, these cyclic substituents being themselves optionally the carriers of 1, 2, 3, 4 or 5 identical or different R$_0$ radicals, R$_0$ having the meanings stated above for the substituents of the aromatic hydrocarbon radical of general formula (V').

Mention may be made, as examples of such radicals, of, inter alia, the benzyl radical.

In the general formula (V) of the carboxylic acids, R$_1$ to R$_4$ can also represent a saturated or unsaturated heterocyclic radical containing in particular 5 or 6 atoms in the ring, including 1 or 2 heteroatoms, such as nitrogen, sulphur and oxygen atoms; it being possible for the carbon atoms of the heterocycle optionally to be substituted, in their entirety or for only a portion of them, by R$_0$ radicals, R$_0$ having the meanings stated above for the substituents of the aromatic hydrocarbon radical of general formula (V').

R$_1$ to R$_4$ can also represent a polycyclic heterocyclic radical defined as being either a radical composed of at least 2 aromatic or non-aromatic heterocycles containing at least one heteroatom in each ring and forming between them ortho- or ortho- and peri-fused systems or either a radical composed of at least one aromatic or non-aromatic hydrocarbon ring and at least one aromatic or non-aromatic heterocycle forming between them ortho- or ortho- and peri-fused systems; it being possible for the carbon atoms of the said rings optionally to be substituted, in their entirety or for only a portion of them, by R$_0$ radicals, R$_0$ having the meanings stated above for the substituents of the aromatic hydrocarbon radical of general formula (V').

Mention may be made, as examples of R$_1$ to R$_4$ groups of heterocyclic type, of, inter alia, furyl, pyrrolyl, thienyl, isoxazolyl, furazanyl, isothiazolyl, imidazolyl, pyrazolyl, pyridyl, pyridazinyl, pyrimidinyl and pyranyl radicals and quinolyl, naphthyridinyl, benzopyranyl, benzofuranyl and indolyl radicals.

It is also possible that, among the R$_1$ to R$_3$ radicals, one of them represents a functional group and mention may in particular be made of functional groups of NR$_9$R'$_9$ type in which R$_9$ and R'$_9$, which are identical or different, represent a hydrogen atom, a linear or branched alkyl group having from 1 to 12 carbon atoms, a phenyl group, a benzyl group or an acyl group having from 2 to 12 carbon atoms, preferably an acetyl or benzoyl group.

Mention may be made, as more specific example, of, inter alia, 2-methyl-2-butenoic acid.

A first class of substrates to which the process of the invention more preferentially applies are substituted acrylic acids which are precursors of amino acids and/or derivatives.

The term substituted acrylic acids is understood to mean all compounds where the formula derives from that of acrylic acid and where two at most of the hydrogen atoms carried by the ethylenic carbon atoms are substituted by a hydrocarbon group or by a functional group.

They can be symbolized by the following chemical formula:

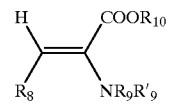

(Va)

in the said formula (Va):

R$_9$ and R'$_9$, which are identical or different, represent a hydrogen atom, a linear or branched alkyl group having from 1 to 12 carbon atoms, a phenyl group or an acyl group having from 2 to 12 carbon atoms, preferably an acetyl or benzoyl group, R$_8$ represents a hydrogen atom, an alkyl group having from 1 to 12 carbon atoms, a cycloalkyl radical having from 3 to 8 carbon atoms, an arylalkyl radical having from 6 to 12 carbon atoms, an aryl radical having from 6 to 12 carbon atoms or a heterocyclic radical having from 4 to 7 carbon atoms, R$_{10}$ represents a hydrogen atom or a linear or branched alkyl group having from 1 to 4 carbon atoms.

Mention may be made, as more specific examples of R$_8$ groups, of an alkyl group, such as methyl, ethyl, isopropyl or isobutyl; a cycloalkyl group, such as cyclopentyl or cyclohexyl; an aromatic group, such as phenyl or naphthyl, or a heterocyclic group, such as furyl, pyranyl, benzopyranyl, pyrrolyl, pyridyl or indolyl.

The R$_{10}$ group is preferentially a hydrogen atom.

Mention may be made, among substituted acrylic acids which are precursors of amino acids, of N-acetyl-α-amino-β-phenylacrylic acid, N-benzoyl-α-amino-β-phenylacrylic acid, in which the phenyl ring is optionally substituted by one or a number of alkyl, alkyloxy or hydroxyl groups, N-acetyl-α-amino-β-indolylacrylic acid, N-benzoyl-α-amino-β-indolylacrylic acid or N-acetyl-α-amino-β-isobutylacrylic acid.

Mention may more particularly be made of:
methyl α-acetamidocinnamate,
methyl acetamidoacrylate,
benzamidocinnamic acid,
α-acetamidocinnamic acid.

The invention also applies, entirely satisfactorily, to carrying out the hydrogenation of itaconic acid and/or derivative and more specifically to the compounds corresponding to the formula (Vb):

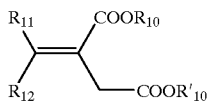

in the said formula (Vb):

R$_{11}$ and R$_{12}$, which are identical or different, represent a hydrogen atom, a linear or branched alkyl group having from 1 to 12 carbon atoms, a cycloalkyl radical having from 3 to 8 carbon atoms, an arylalkyl radical having from 6 to 12 carbon atoms, an aryl radical having from 6 to 12 carbon atoms or a heterocyclic radical having from 4 to 7 carbon atoms, R$_{10}$ and R'$_{10}$, which are identical or different, represent a hydrogen atom or a linear or branched alkyl group having from I to 4 carbon atoms.

The preferred substrates correspond to the formula (Vb) in which R$_{11}$ and R$_{121}$ which are identical or different, represent a hydrogen atom or an alkyl group having from 1 to 4 carbon atoms and R$_{10}$ and R'$_{10}$, which are identical or different, represent a hydrogen atom or a methyl group.

Mention may be made, as more specific examples, of in particular itaconic acid and dimethyl itaconate.

The process of the invention applies very particularly to the preparation of arylpropionic acids by hydrogenation of a substrate corresponding to the formula (Vc):

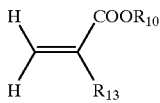

in the said formula (Vc):
R$_{10}$ represents a hydrogen atom or a linear or branched alkyl group having from 1 to 4 carbon atoms,
R$_{13}$ represents a phenyl or naphthyl group, optionally carrying a substituent or a number of substituents R:
R can represent R$_0$, one of the following groups:
a linear or branched alkyl or alkenyl group having from 1 to 12 carbon atoms, preferably a linear or branched alkyl group having from 1 to 4 carbon atoms,
a linear or branched alkoxy group having from 1 to 12 carbon atoms, preferably a linear or branched alkoxy group having from 1 to 4 carbon atoms,
a linear or branched alkoxy group having from 2 to 8 carbon atoms, preferably an acetoxy group,
a linear or branched acylamido group having from 1 to 8 carbon atoms, preferably an acetamido group,
an NO$_2$ group,
R can represent R$_0$', one of the following, more complex groups:
a group of formula

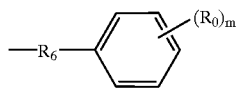

in which:
R$_6$ represents a valence bond; a saturated or unsaturated, linear or branched, divalent hydrocarbon group having from 1 to 6 carbon atoms such as, for example, methylene, ethylene, propylene, isopropylene or isopropylidene or one of the following groups known as Z:
—O—; —CO—; —COO—; —NR$_7$—; —CO—NR$_7$—; —S—; —SO$_2$— or —NR$_7$—CO—;
in the said formulae R$_7$ represents a hydrogen atom or a linear or branched alkyl group having from 1 to 6 carbon atoms,
R$_0$ has the meaning given above,
m is an integer from 0 to 4.

Mention may be made, as specific examples, of 2-(3-benzoylphenyl)propionic acid (Ketoprofen®), 2-(4-isobutylphenyl)propionic acid (Ibuprofen®) or 2-(5-methoxynaphthyl)propionic acid (Naproxen®).

The selective asymmetric hydrogenation of the said substrates is carried out by using, as catalysts, the metal complexes of the invention containing the optically active diphosphine ligands of general formula (Ia) or (Ib).

When the diphosphine-transition metal complexes of the invention are used as catalysts for the asymmetric hydrogenation of unsaturated carboxylic acids, the desired product can be obtained with a high optical yield.

By choosing one of the optical isomers of the diphosphine having a (+) or (−) optical rotation and by using a diphosphine-transition metal complex comprising the chosen isomer, the unsaturated carboxylic acid is hydrogenated to a compound having the desired absolute configuration with a high optical yield.

The hydrogenation is generally carried out at a temperature of between 20 and 100° C.

The hydrogen pressure can be between 0.1 and 200 bar and more preferentially between 1 and 150 bar.

The diphosphine/transition metal complex is used 80 that the ratio of the number of atoms of metal present in the complex to the number of moles of the compound to be hydrogenated is between 0.1 and 0.0001.

The hydrogenation process is preferably implemented in an organic solvent. Any solvent is used, in so far as it is stable under the reaction conditions.

A polar organic solvent is preferably used and more particularly the following solvents:
aliphatic, cycloaliphatic or aromatic ethers and, more particularly, diethyl ether, dipropyl ether, diisopropyl ether, dibutyl ether, methyl tert-butyl ether, di-tert-butyl ether, ethylene glycol dimethyl ether or the dimethyl ether of diethylene glycol; diphenyl ether, dibenzyl ether, anisole, phenetole, 1,4-dimethoxybenzene or veratrole; or 1,4-dioxane or tetrahydrofuran (THF),
mono- or polyhydroxylated alcohols and more particularly aliphatic monoalcohols such as methanol, ethanol, propanol, butanol, sec-butanol, tert-butanol, pentanol or hexanol; aliphatic dialcohols such as ethylene glycol, diethylene glycol or propylene glycol; or cycloaliphatic alcohols such as cyclopentanol or cyclohexanol,
aliphatic ketones such as acetone, methyl ethyl ketone or diethyl ketone,
aliphatic esters such as in particular methyl acetate, ethyl acetate or propyl acetate.

The concentration of the substrate in the organic solvent advantageously varies between 0.01 and 1 mol/l.

After the formation of the hydrogenation complex, a basic compound can optionally be added.

This basic compound can be an alkali metal base, such as sodium or potassium hydroxide, or else a primary, secondary or tertiary amine and more particularly pyridine, piperidine or triethylamine and preferably triethylamine.

The amount of base added is such that the ratio of the number of moles of base to the number of metal atoms present in the diphosphine/transition metal complex is between 0 and 25 and preferably between 0 and 12.

A preferential embodiment of the process of the invention is given hereinbelow.

The said process is implemented in an autoclave which is purged using an inert gas, preferably nitrogen. Charging is preferably carried out of the substrate in solution in the organic solvent and then of the catalyst, also in solution in the organic solvent.

The nitrogen is replaced by hydrogen.

The hydrogenation is completed when the hydrogen pressure becomes stable.

The hydrogenation process according to the invention allows access, with high enantiomeric excesses, to different enantiomers of many derivatives.

The following examples, given without implied limitation, illustrate the present invention.

An implementational example of the present invention is given hereinbelow by way of illustration, without any limiting nature.

Example 1 relates to the preparation of the new optically active (S,S)-(+)- and (R,R)-(−) -bis [1-phospha-2,3-diphenyl-4,5-dimethylnorbornadiene] diphosphines.

In Examples 2 to 4, the synthesis of the catalysts used in hydrogenation is described.

Examples 5 to 13 correspond to the applicational examples.

EXAMPLES

Example 1

Phospholyllithium: (III)

11.3 g (0.06 mol) of 1-phenyl-3,4-dimethylphosphole, 0.8 g of lithium metal and 100 ml of distilled tetrahydrofuran are introduced into a 250 ml round-bottomed flask.

The mixture is stirred under argon for 2 hours in a cold water bath.

The solution becomes brown.

The appearance of the phospholyllithium is monitored by $^{31}$P NMR.

$^{31}$P NMR=δ(THF)=55.8 ppm.

Is order to trap the phenyllithium, 2.7 g of aluminium chloride are added at 0° C.

The mixture is allowed to react for 30 minutes at 0° C.
1,1′-Bisphosphole: (IV)

6 g (0.025 mol) of diiodine, in solution in 25 ml of tetrahydrofuran, are added dropwise at ambient temperature to the above mixture.

When 90% of this solution is introduced, the disappearance of (III) is confirmed by $^{31}$P NMR.

$^{31}$P NMR=δ(THF)=−22.4 ppm.

The 1,1′-bisphosphole (IV) is extracted under nitrogen from the mixture using hexane.
Bis[1-phospha-2,3-diphenyl-4,5-dimethylnorbornadiene]: (I m) and (I r)

The above solution is evaporated to dryness, with air excluded and brought to 140° C.

8 g of diphenylacetylene are then introduced and the reaction mixture is allowed to react for 15 to 20 minutes.

The disappearance of (IV) is again monitored by $^{31}$P NMR.

The spectrum is composed of 2 singlets corresponding to the two diastereoisomers.

The product is extracted with ether and washed with water.

The organic phases are combined and then evaporated to dryness.

The residue is then purified by chromatography on a silica column (elution with hexane to remove the excess diphenylacetylene and then with a hexane/dichloromethane: 80/20 by volume mixture).

The overall yield is 30%.

Complex of palladium(II) with (I m) and (I r): (VI m) and (VI r)

5 g (8.25 mmol) of (I m) and of (I r) are introduced into a 500 ml round-bottomed flask and are dissolved in 200 ml of dichloromethane.

3 g (8.25 mmol) of PdCl$_2$(PhCN)$_2$ in 100 ml of dichloromethane are then added dropwise.

The reaction, carried out under argon, is immediate.

The solution is evaporated to dryness and the residue is subjected to chromatography on silica in order to separate the two diastereoisomers.

Elution is carried out using dichloromethane in order to remove the impurities, then with a mixture of dichloromethane and ethyl acetate: 95/5 by volume in order to separate the racemate and finally with a dichloromethane/ethyl acetate: 80/20 by volume mixture in order to separate the meso.

$^{31}$P NMR=δ(CH$_2$Cl$_2$)=81.9 ppm—minor isomer corresponding to the racemate.

$^{31}$P NMR=δ(CH$_2$Cl$_2$)=88.1 ppm—major isomer corresponding to the meso.

Decomplexation of (VI r)

1.5 g (0.002 mol) of racemic (VI r) and 20 ml of dichloromethane are introduced into a 100 ml round-bottomed flask.

0.5 g of sodium cyanide and a few milliliters of water (3 ml) are then added.

The mixture is stirred vigorously under argon for 10 to 15 minutes.

The bis[1-phospha-2,3-diphenyl-4,5-dimethylnorbornadiene] (I r) is then extracted with dichloromethane.

The organic phase is washed with water and then dried over sodium sulphate.

Pure (I r) is thus recovered.

The overall yield of the separation of the diastereoisomers is 90%.

The characterization of the racemic mixture (I r) is as follows:

$^{31}$P NMR=δ(CDCl$_3$)=−13.2 ppm.

$^1$H NMR=δ(CDCl$_3$)=1.31 (a, 6H, CH$_3$), 1.69

(s, 6H, CH$_3$), 2.02–2.20 (m, 4R, CH$_2$ bridge), 6.86–7.29 (m, 20H, phenyl protons).

Binuclear palladium(II) complex:

290 mg (0.5 mmol) of racemic (I r) and 300 mg (0.5 mmol) of (+)-di-µ-chlorobis{2-[1-(dimethyl-amino)ethyl]phenyl-C,N}dipalladium are introduced under nitrogen into 12 ml of benzene.

Complexation is rapid and monitored by $^{31}$P NMR.

The brown solution is evaporated to dryness and the residue chromatographed in order to separate the two diastereoisomers (toluene/ethyl acetate:80/20 by volume elution).

The two pure isolated enantiomers are thus recovered in the form of two diastereoisomer complexes of formula:

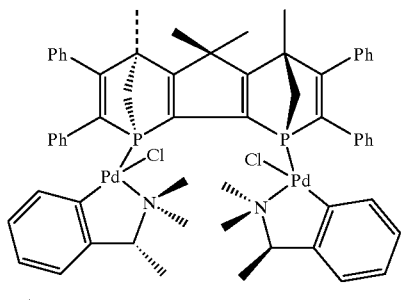

and

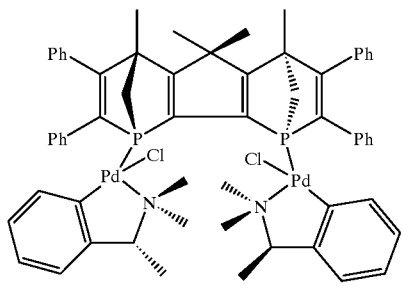

These enantiomers are recovered pure by decomplexing as for (VI r).

The diphosphines of formulae (Ia) and (Ib) respectively are identified as follows:

$^{31}$P NMR=δ(CDCl$_3$)=−13.2 ppm; $[α]_D$ =+231° (c=1, C$_6$D$_6$).

$^{31}$P NMR δ(CDCl$_3$)-=13.2 ppm; $[α]_D$=−198° (c=1, C$_6$D$_6$)

(with an $[α]_D$ determined for a concentration of 10 mg/ml and at ambient temperature).

Example 2

In this example, the preparation of a complex of formula [Rh$^+$(COD)(P*P)]PF$_6^-$, in which COD represents 1,5-cyclooctadiene and (P*P) represents the diphosphine of formula (Ib), is described.

11.6 mg of Rh(COD)$_2$PF$_6$ are dissolved, under argon, in 3 ml of acetone in a 10 ml Schlenk flask.

A solution of 7.5 mg of the said diphosphine in acetone in then added dropwise, still under an inert gas.

After stirring for a few minutes, the expected complex is obtained.

$^{31}$P NMR: δ=73.8 ppm, J(Rh-P)=155 Hz.

Example 3

In this example, the preparation of a complex of formula [Rh$^+$(COD)(P*P)]PF$_6^-$ in which COD represents 1,5-cyclooctadiene and (P*P) represents the diphosphine of formula (Ia), is described.

The said complex is prepared according to the same procedure as that of Example 2.

Example 4

In this example, the preparation of a complex of formula RuBr$_2$(P*P), in which (P*P) represents the diphosphine of formula (Ia): is described.

7.5 mg of diphosphine and 4 mg of Ru(COD)(allyl)$_2$ are dissolved, under argon, in 2 ml of acetone in a 10 ml Schlenk flask.

0.11 ml of a 0.29M aqueous hydrobromic acid solution in methanol is then added dropwise.

Stirring is carried out for 30 min at ambient temperature (−20° C.) and the expected complex is obtained.

$^{31}$P NMR: AB system, δ98.2 ppm, 88.1 ppm (J$_{AB}$=21 Hz).

Example 5

In this example, the asymmetric hydrogenation is carried out, using the catalyst of Example 2, of the following compound:

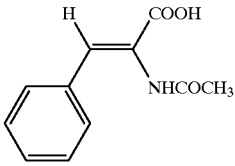

400 mg of the said compound are dissolved in 20 ml of methanol in a round-bottomed flask.

The complex 1 of Example 2 is then prepared as proposed above.

The acetone is evaporated and the residue is dissolved in 5 ml of methanol.

The 2 solutions are then introduced into an autoclave which has been purged beforehand and maintained under a nitrogen atmosphere.

Hydrogen is then introduced to a pressure of 3 atmospheres.

Agitation is carried out at 20° C. for 1 h.

The excess hydrogen is discharged and the reaction solution is recovered.

The solvent is evaporated and the residue analysed by $^1$H NMR in order to confirm the progress of the reaction.

The reaction is quantitative.

The enantiomeric excess is determined by chiral high performance liquid chromatography (Shandon®, 150×6.4 mm, HSA protein chiral column) and the absolute configuration of the product by measurement of the $[α]_D$ and by polarimetry.

With the diphosphine (Ib), ee≧98%, $[α]_D$ (ethanol, c=1) >0.

Example 6

In this example, the asymmetric hydrogenation is carried out, using the catalyst of Example 4, of the following compound:

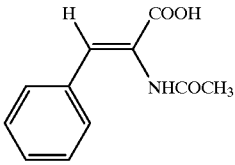

The implementation is the same as with 1. The difference lies in the catalyst, the reaction time is less than 24 hours and the pressure atmospheric.

With the diphosphine (Ia), ee=80%, $[\alpha]_D$ (ethanol, c=1) <0.

Example 7

In this example, the asymmetric hydrogenation is carried out, using the catalyst of Example 3, of the following compound:

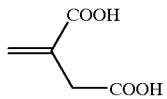

The implementation is identical.

165 mg of itaconic acid are introduced, still with the same amount of solvent and of catalyst.

The reaction is carried out at ambient temperature, in less than 3 hours.

With the diphosphine (Ia), ee=80%, $[\alpha]_D$ (ethanol, c=2.16)<0.

Example 8

In this example, the asymmetric hydrogenation is carried out, using the catalyst of Example 2, of the following compound:

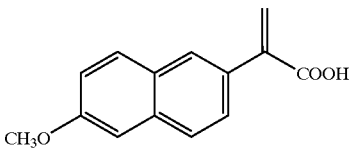

245 mg of the said compound are dissolved in 8 ml of methanol in a flask.

The complex 1 of Example 2 is then prepared as proposed above.

The acetone is evaporated and the residue is dissolved in 2 ml of methanol.

This solution is then introduced into the flask, which is itself placed in the autoclave which has been purged beforehand and maintained under an argon atmosphere.

Hydrogen is then introduced to a pressure of 4 atmospheres.

Agitation is carried out at 20° C. for 2 hours.

The excess hydrogen is discharged and the reaction solution is recovered.

The reaction solution is evaporated and the residue analysed by 1H NMR in order to confirm the progress of the reaction.

The progress is 30%.

The enantiomeric excess (ee) is determined by chiral high performance liquid chromatography (Chiral pack-AD column).

With the diphosphine (Ib), ee>98%.

Example 9

In this example, the preparation of a complex of formula Ru(OAc)$_2$(P*P), in which OAc represents an acetate group and (P*P) the diphosphine of formula (Ib), is described.

10 mg of diphosphine (Ib) and 6 mg of Ru(Me-allyl)$_2$(COD) are dissolved, under argon, in 2 ml of acetone in a 10 ml Schlenk flask.

A solution of 4 mg of CCl$_3$CO$_2$H in 1 ml of methanol is then added dropwise.

After stirring for a few minutes, a large excess of sodium acetate, dissolved in 1 ml of methanol, is added and the expected complex is obtained after stirring for a few minutes.

$^{31}$P NMR: $\delta$=107.9 ppm

Example 10

In this example, the preparation of a complex of formula Ru(OAc)$_2$(P*P), in which OAc represents an acetate group and (P*P) the diphosphine of formula (Ia), is described.

The said complex is prepared according to the procedure of Example 9.

Example 11

In this example, the asymmetric hydrogenation is carried out, using the catalyst of Example 9, of the following compound:

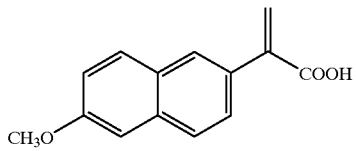

The implementation is the same as in Example 8. The difference lies in the catalyst, the reaction time, which is 12 hours, and the pressure of 130 atmospheres. The progress is 12%.

With the diphosphine (Ib), ee>95%.

Example 12

In this example, the asymmetric hydrogenation is carried out, using the catalyst of Example 10, of the following compound:

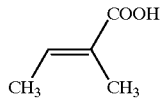

100 mg of the said compound, are dissolved in 4 ml of methanol in a round-bottomed flask.

The complex of Example 9 is then prepared as proposed above.

The two solutions are then introduced into an autoclave which has been purged beforehand and maintained under a nitrogen atmosphere.

Hydrogen is then introduced to a pressure of 4 atmospheres.

Agitation is carried out at 20° C. for 3 hours.

The excess hydrogen is discharged and the reaction solution is recovered.

The solution is evaporated and the residue analysed by $^1$H NMR in order to confirm the progress of the reaction.

The progress is 90%.

The enantiomeric excess (ee) is determined by chiral high performance liquid chromatography (Chiral cell —OJ—R column).

With the diphosphine (Ia), ee=57%.

Example 13

In this example, the asymmetric hydrogenation is carried out, using the catalyst of Example 2, of the following compound:

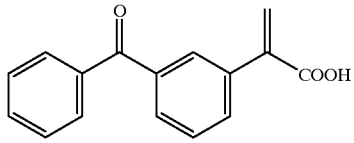

270 mg of the said compound are dissolved in 8 ml of methanol in a flask.

The complex 1 of Example 2 is then prepared as proposed above.

The acetone is evaporated and the residue is dissolved in 3 ml of methanol.

This solution is then introduced into the flask, which is itself placed in the autoclave which has been purged beforehand and maintained under an argon atmosphere.

Hydrogen is then introduced to a pressure of 5 atmospheres.

Agitation is carried out at 20° C. for 2 hours.

The excess hydrogen is discharged and the reaction solution is recovered.

The reaction solution is evaporated and the residue analysed by $^1$H NMR in order to confirm the progress of the reaction.

The progress is 70%.

The enantiomeric excess (ee) is determined by chiral high performance liquid chromatography (Chiral cell —OJ—R column).

With the diphosphine (Ib), ee>98%.

We claim:

1. Process for the preparation of an optically active carboxylic acid and/or ester, wherein an α,β-unsaturated carboxylic acid and/or an ester thereof is/are asymmetrically hydrogenated in the presence of an effective amount of a metal complex comprising, as ligand, the optically active diphosphine of formula (Ia)

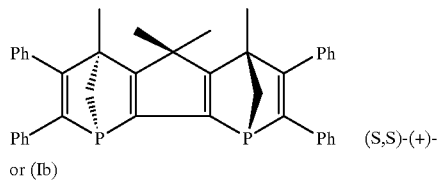 (S,S)-(+)- or (Ib)

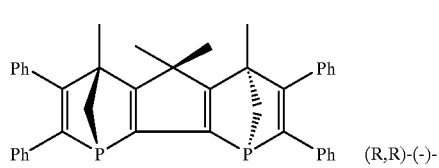 (R,R)-(-)- and a transition metal.

2. Process according to claim 1, wherein the α,β-unsaturated carboxylic acid and/or ester corresponds to the following general formula:

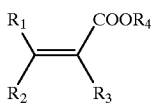 (V)

in said formula (V):

$R_1$, $R_2$, $R_3$ and $R_4$ represents a hydrogen atom or any hydrocarbon group.

3. Process according to claim 2, wherein the α,β-unsaturated carboxylic acid and/or ester thereof corresponds to the formula (V) in which the $R_1$ to $R_4$ radicals, which are identical or different, represent an optionally substituted hydrocarbon radical having form 1 to 20 carbon atoms which is a linear or branched, saturated or unsaturated, acyclic aliphatic radical; a monocyclic or polycyclic, saturated, unsaturated or aromatic, heterocyclic or carbocyclic radical; or a linear or branched, saturated or unsaturated, aliphatic radical carrying a cyclic substituent.

4. Process according to claim 1, wherein the carboxylic acid used in a substituted acrylic acid which is a precursor of an amino acid.

5. Process according to claim 4, wherein the carboxylic acid used is a substituted acrylic acid which is a precursor of an amino acid and/or ester corresponding to the following formula:

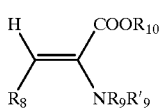 (Va)

in said formula (Va):

$R_9$ and $R'_9$, which are identical or different, represent a hydrogen atom, a linear or branched alkyl group having from 1 to 12 carbon atoms, a phenyl group or an acyl group having from 2 to 12 carbon atoms, $R_8$ represents a hydrogen atom, an alkyl group having from 1 to 12 carbon atoms, a cycloalkyl radical having from 3 to 8 carbon atoms, an arylalkyl radical having from 6 to 12 carbon atoms, an aryl radical having from 6 to 12 carbon atoms or a heterocyclic radical having from 4 to 7 carbon atoms, $R_{10}$ represents a hydrogen atom or a linear or branched alkyl group having from 1 to 4 carbon atoms.

6. Process according to claim 4, wherein the carboxylic acid used is N-acetyl-α-amino-β-phenylacrylic acid or, N-benzoyl-α-amino-β-phenylacrylic acid, in which the phenyl ring is optionally substituted by one or a number of alkyl, alkyloxy or hydroxyl groups, N-acetyl-α-amino-β-indolylacrylic acid, N-benzoyl-α-amino-β-indolylacrylic acid or N-acetyl-α-amino-β-isobutylacrylic acid.

7. Process according to claim 1, wherein the carboxylic acid used is itaconic acid and/or ester corresponding to the following formula:

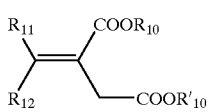 (Vb)

in said formula (Vb):

$R_{11}$ and $R_{12}$, which are identical or different, represent a hydrogen atom, a linear or branched alkyl group having from 1 to 12 carbon atoms, a cycloalkyl radical having from 3 to 8 carbon atoms, an arylalkyl radical having from 6 to 12 carbon atoms, an aryl radical having from 6 to 12 carbon atoms or a heterocyclic radical having from 4 to 7 carbon atoms, $R_{10}$ and $R_{11}$, which are identical or different, represent a hydrogen atom or a linear or branched alkyl group having from 1 to 4 carbon atoms.

8. Process according to claim 7, wherein the carboxylic acid used is itaconic acid or dimethyl itaconate.

9. Process according to claim 1, wherein the carboxylic acid used is an arylpropionic acid and/or ester thereof corresponding to the following formula:

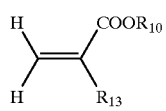

(Vc)

in said formula (Vc):

$R_{10}$ represents a hydrogen atom or a linear or branched alkyl group having from 1 to 4 carbon atoms, $R_{13}$ represents a phenyl or naphthyl group, optionally carrying one or more substituents.

10. Process according to claim 9, wherein the carboxylic acid used is 2-(3-benzoylphenyl)propionic acid, 2-(4-isobutylphenyl)propionic acid or 2-(5-methoxynaphthyl)propionic acid.

11. Process according to claim 1, wherein the hydrogenation is carried out at a temperature of between 20 and 100° C.

12. Process according to claim 1, wherein the hydrogen pressure is between 0.1 and 200 bar.

13. Process according to claim 1, wherein use is made of at least one metal complex.

14. Process according to claim 1, wherein the ratio of the number of atoms of metal present in the complex to the number of moles of the compound to be hydrogenated is between 0.1 and 0.0001.

15. Process according to claim 1, wherein after a formation of the hydrogenation complex, a basic compound is added.

* * * * *